United States Patent [19]

Smith et al.

[11] 4,292,920
[45] Oct. 6, 1981

[54] MAGNETIC ATTRACTION TRANSFER DEVICES FOR USE IN SOLID PHASE RADIOIMMUNOASSAYS AND IN OTHER ASSAY METHODS

[76] Inventors: Kendall O. Smith, 133 Trillium La., San Antonio, Tex. 78312; Warren D. Gehle, 6815 Forest Haven, San Antonio, Tex. 78240

[21] Appl. No.: 105,707

[22] Filed: Dec. 20, 1979

Related U.S. Application Data

[62] Division of Ser. No. 680,506, Apr. 26, 1976, abandoned.

[51] Int. Cl.³ .............................................. B05C 3/00
[52] U.S. Cl. ..................................... 118/425; 118/500
[58] Field of Search ....................... 118/400, 425, 500

Primary Examiner—Bernard D. Pianalto
Attorney, Agent, or Firm—Watson, Cole, Grindle & Watson

[57] ABSTRACT

A device for transferring, by magnetic attraction, antigen-antibody adsorbent materials from one reaction mixture to another, and to facilitate an efficient rinsing of these materials, and for transferring adsorbent materials used in other assay methods.

12 Claims, 10 Drawing Figures

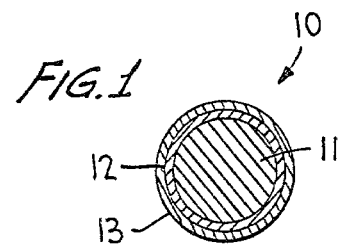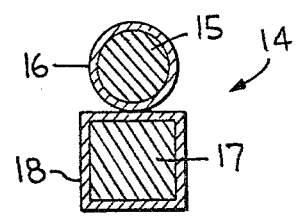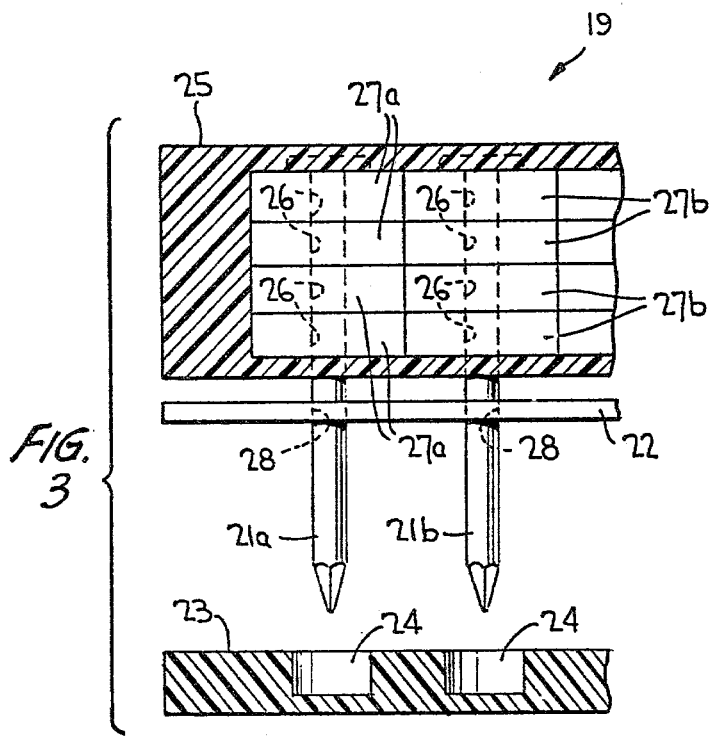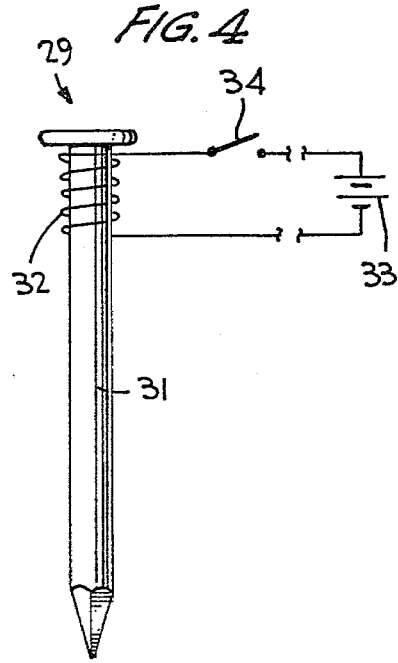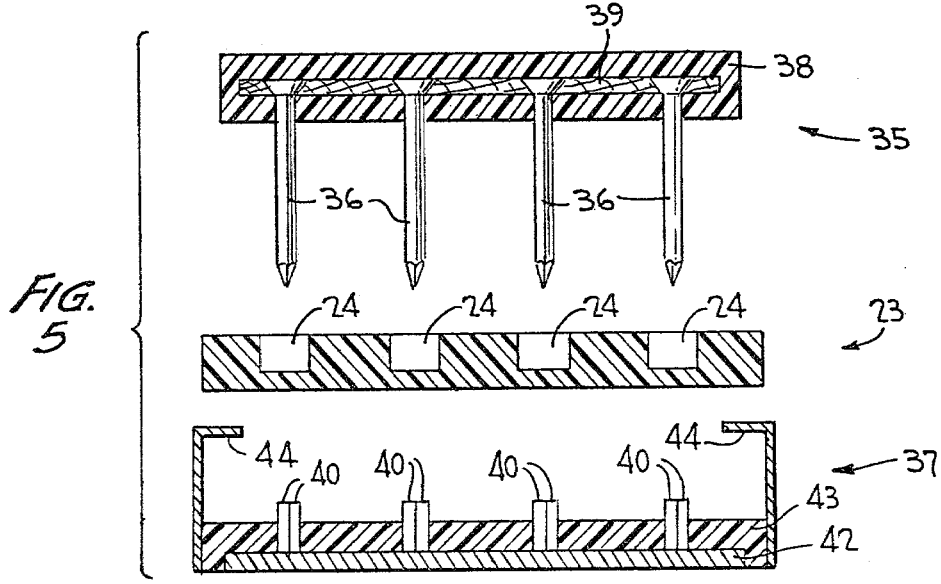

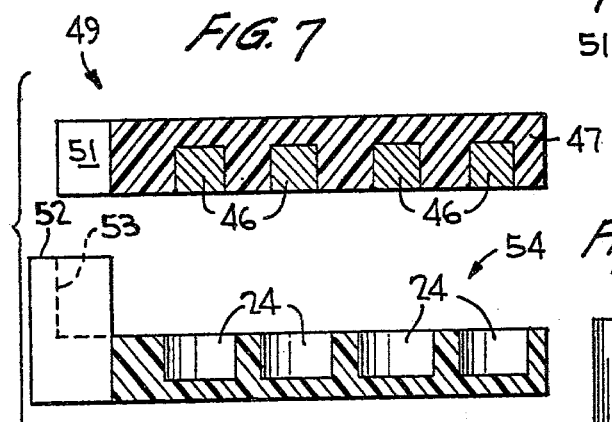
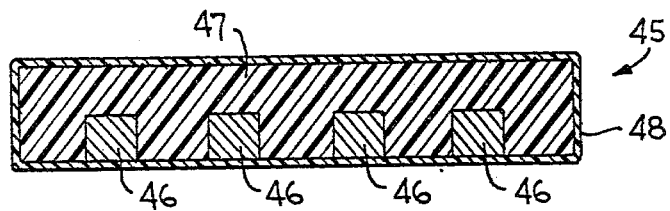
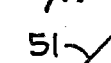
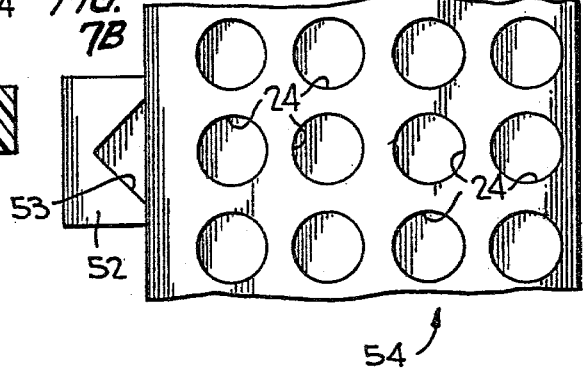
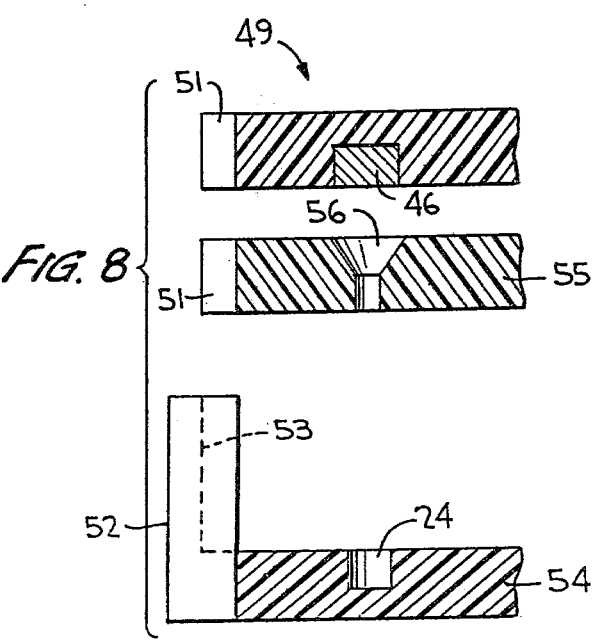

MAGNETIC ATTRACTION TRANSFER DEVICES FOR USE IN SOLID PHASE RADIOIMMUNOASSAYS AND IN OTHER ASSAY METHODS This is a divisional of application Ser. No. 680,506 filed Apr. 26, 1976 now abandoned.

BACKGROUND OF THE INVENTION

Radioimmunoassay (RIA) methods generally fall into two categories: liquid and solid phase. Liquid phase methods, which involve immune complexes in the form of precipitates suspended in a liquid phase, have been widely used for detection and quantitation of protein containing antigens, including hormones and viruses. However, solid phase methods are enjoying more widespread use, particularly for detecting and quantitating viral antigens and anitbodies. The solid phase may involve surface areas in test tubes (U.S. Pat. No. 3,867,517), in depression plates, on beads, or any other convenience device (U.S. Pat. No. 3,826,619) whose surfaces are of a composition which will adsorb the antigen or antibody reactants and which are of a size and shape which will fit into a gamma counter (see also *Journal of Immunological Methods*, Vol. 5 (1974) pp. 337-344). Advantages in using solid phase RIA systems include the capability for efficient rinsing and transferring of the solid phase, with the antigen-antibody complexes on its surface, without the requirement for centrifugation-resuspension of antigen-antibody precipitates required in most liquid phase methods.

Spherical beads are particularly useful as solid phases (see *Journal of Clinical Microbiology*, August 1975, pp. 130-133) because beads can be obtained with extremely uniform diameters (hence surface areas); they each contact the bottom of a container at only one small point, they can be totally immersed in reagent solutions and, for these reasons, give highly reproducible results in RIA procedures. Such precision is difficult to obtain with inner surfaces of test tubes or depression plate wells, probably because: reactants adsorb to the surfaces of these vessels to various heights during slight "sloshing" attendant with movements of the vessels; splashing of reagents sequentially added during the test and streaming of reagents down the vessels' sides occur during their delivery. Therefore, unfortunate variations in the surface areas exposed to reagents are inevitable. Immersed beads, on the other hand, allow high uniformity of surface areas exposed to reagents and, when totally immersed, exposure of this uniform surface is highly reproducible and results in high RIA precision. As examples of the superiority of the bead solid phase system for RIA over tube solid phase systems, the test for Australia antigen has been heretofore converted from the tube to the bead test, and bead tests are the only ones currently licensed for use in the United States for detection of hepatitis B antigen in blood donors' sera.

Processing and transferring beads by the presently used methods, however, leaves much to be desired. The use of forceps (page 339, *Journal of Immunological Methods*, supra) to transfer each bead separately is tedious, time consuming and subject to inadvertent small variations inevitable when handling is manual. These deficiencies significantly limit the usefulness of bead assay methods because: (1) the number of assays which can be done at one time under reasonably identical conditions of timing is restricted; (2) small variations in manual handling, especially between different technicians, limit the precision with which assays can be accomplished and may be one of the precision limiting factors in the test; and (3) the cost associated with tedious manual manipulation of many individual beads is substantial.

These problems have been partially solved in a design of a test for hepatitis B antigen by allowing beads to remain in the same depression plate wells throughout the RIA procedure, merely aspirating reagents and rinsing beads in many wells simultaneously with a mechanically sophisticated, manifold type rinsing-dispensing device, then dumping the beads by the force of gravity from the depression plate wells into tubes for insertion into a gamma counter. There are some objections to this procedure, however, when considering optimal test conditions for the hepatitis test and other applications in particular. Performing a RIA bead test completely in one well involves reactions with the well's walls simultaneously with the bead reaction. In effect, then, the well wall surface competes with the bead surface for reagents introduced later in the test. Non-specific adsorption of reactants is usually followed by a small amount of release of reactants into succeeding reagents added, which is unfortunately magnified quantitatively if the same well is used throughout the test. Transferring the beads to new wells during the test with facility would obviate this problem. Aspiration of fluids from small volume cul de sacs containing beads with large surface areas, followed by addition of small volumes of rinsing fluid nevertheless constitutes a relatively inefficient rinsing procedure because of the difficulty in aspirating all of the fluid in the well (a small cul de sac containing an object with a maximum surface area, a sphere, hence attracting maximum fluid volume due to capillary or surface tension effects). Also, this approach does not eliminate the necessity for transferring beads one-at-a-time by forceps into the wells initially. If there are dozens of wells and a short incubation period, treatment of the first and last beads will necessarily be significantly different. Similarly, exact volumes of new reagents must be delivered to each separate well during the RIA process. Thus, beads exposed first during this procedure will not be treated identically to beads exposed at the last of the dispensing period. Therefore, when large numbers of beads are employed in an assay run (as when testing many different specimens) and short reaction periods are desirable (30 minutes, for example), uniformity in test conditions is seriously compromised and the precision of the assay suffers substantially. Inability to expose all beads to the same reagents simultaneously thus limits the usefulness of any RIA procedure, but particularly those procedures involving many specimens, short incubation times and numerous reagents.

SUMMARY OF THE INVENTION

A process and means for carrying it out are provided in accordance with the invention wherein magnetic force is used to move antigen-antibody coated solid phase units from one place to another, i.e., from a predispensed reaction mixture to reaction mixture, into and out of large volumes of rinsing fluids and, finally, to test tubes or vials which are to be inserted into a gamma counter. Coated solid phase units usable in other assay methods may likewise be transferred in accordance with the invention.

It is therefore a principle object of this invention to provide apparatus for use in RIA determinations, or any other chemical reaction in which a solid phase is essential, which allows a high degree of mechanization and temporal exactness in the transfer of the solid phase from one location to another.

Another object of the present invention is to facilitate the processing of large numbers of units simultaneously under extremely uniform conditions, so as to yield highly reproducible results in solid phase assays with large numbers of specimens.

A further object of this invention is to facilitate extremely efficient washing of solid phase units to remove contaminating reactants which decrease the sensitivity and specificity of solid phase analytical systems.

A still further object of this invention is to provide an efficient, yet mechanically simple and trouble-free device for rinsing solid phase units, a requirement of all solid phase methods, thus eliminating the requirement for mechanically more sophisticated, and consequently more expensive aspiration-rinse devices presently in use.

These and other purposes and advantages will become more apparent from the following more detailed description of the invention when taken in conjunction with the accompanying drawings.

BRIEF DESCRIPTION OF THE DRAWINGS

FIG. 1 is a greatly enlarged sectional view of one form of the solid-phase units of the present invention;

FIG. 2 is a greatly enlarged sectional view of a second embodiment of the solid-phase unit of the present invention;

FIG. 3 is an expanded sectional view showing part of one form of the transfer device of the present invention in relation to a test receptacle tray;

FIG. 4 is a perspective view of a second embodiment of the transfer device of the present invention;

FIG. 5 is an expanded sectional view of a third embodiment of the transfer device of the present invention in relation to a test receptacle tray;

FIG. 6 is a sectional view of a fourth embodiment of the transfer device of the present invention;

FIG. 7 is a sectional view of a fifth embodiment of the transfer device and test receptacle tray of the present invention;

FIGS. 7A and 7B are respectively bottom plan and top plan views of the transfer device and tray of FIG. 7; and FIG. 8 is an expanded sectional view of a sixth embodiment of the transfer device of the present invention.

Referring to FIG. 1, a solid-phase unit 10 (hereafter referred to as "unit") of the present invention comprises a core 11 of ferrous metal when used in the embodiments of FIGS. 3 and 4, or a core 11 of magnetic material when used with the embodiment of FIG. 5, for example. The core is coated with a layer 12 to seal its surface and to prevent chemical interactions with the ferrous metal or magnetic core 11, and is further coated with an outer layer of an appropriate adsorbent material 13. Layers 12 and 13 may be unitary and the same if composed of a material that can act as both a sealant and as an adsorbent. The unit may be of various shapes, sizes and colors, although a sphere with a diameter range of from about 0.1 mm to about 2.0 cm is preferred because of the increased surface-to-volume ratio and the ease of handling a plurality of such units.

Referring to FIG. 2, the second embodiment of a unit 14 of the present invention comprises a non-ferrous metal, non-magnetic component 15 of adsorbent material (or a non-ferrous metal, non-magnetic compound 15 coated with a layer of adsorbent material 16) joined in any suitable manner as by adhesive bonding to a ferrous metal or magnetic component 17 coated with a layer 18 to seal its surface and to prevent chemical interaction similarly as described with reference to FIG. 1. Unit 14 is used when it is difficult or inconvenient to apply a suitable adsorbent layer to the ferrous metal or magnetic material.

Any number of different types of undercoatings 12 and 18 can be applied to the ferrous metal or magnetic material in order to seal the surface and thus to prevent unwanted chemical reactions from taking place with the ferrous metal or magnetic core 11 and 17. Among these coatings are conventional waterproof primer or sealant paints normally used as base coats for subsequent layers of paint. Required characteristics of this undercoating are that the coating be waterproof, resistant to rapid degradation by dilute salt (such as NaCl) solutions, and compatible with the susequent application of a surface layer of adsorbent material 13. Other efficient coatings 12 and 18, which fulfill these requirements, are a metal coating such as nickel, zinc, chromium, cadmium, copper, gold or any other metal relatively resistant to oxidation or chemical degradation by dilute aqueous solutions of salts to thereby effectively seal the core from penetration and chemical interaction with various aqueous salt solutions.

Any number of different types of surface coatings 13 and 16 can be applied, the choice of coating being dependent upon the type of RIA determination to be performed and consequently the nature of the materials to be adsorbed to the unit. Among these coatings may be various plastics (acrylics, polycarbonate, polyethylene, polystyrene, polypropylene, etc.), glass, chromatographic substances or any other material which will adhere to the surface and allow adequate adsorption of reactants in a particular test system. Plastic surfaces (with or without pigments) may be readily applied by dipping or spraying, using a solution of the plastic in an appropriate solvent, and allowing the solvent to dry. The choice of ssolvents and the method of application must be such as to be compatible with the integrity of layer 12.

The size and shape of the units is not critical except that they should be as uniform as possible in surface area and not be of a design consisting of deep cul de sacs or which would cause difficulty in uniform exposure of all parts of the unit's surface area to reaction mixtures and washing.

Units can be color-coded (distincitve color coats) or shape-coded (distinctive shapes) so as to allow processing of several different kinds of units together, in the same test receptacle, and to allow transfer of several units by a single probe at one time in a manner which will become more apparent hereinafter. In this way, several different antigen-antibody reactions can be accomplished simultaneously in the same test receptacle, with the particular unit identified by color or shape. This color coding can be achieved easily by selection of pigments to be incorporated into sealant coating 12, or by use of different metal plating having characteristic colors.

A preferred embodiment of unit 10 of FIG. 1 is a ferrous metal sphere 0.33 mm in diameter (a Crosman BB) coated with sealant paint, or cadmium, and overlayed with polycarbonate. A preferred embodiment of unit 14 of FIG. 2 is an imitation pearl 6 mm in diameter bonded with epoxy to a ¼"×¼" ceramic magnet coated with sealant paint.

Referring to FIG. 3, a transfer device 19 of the present invention comprises at least one magnetic probe 21 capable of transferring at least one unit which adheres to the probe, and a member 22 for removing the unit from the probe. Associated with the transfer device is a non-ferrous test receptacle tray 23 having at least one test receptacle or well 24 for each magnetic probe.

A preferred embodiment of the transfer device of FIG. 3 includes a body 25 having twenty (only two shown) sixteen-penny common nails 21 projecting outwardly thereof as shown. Each nail extends through 3/16" centrally located holes 26 in four ⅞"×5/16"×¼" ceramic permanent magnet discs 27. Each magnet has a ⅛ lb. lift. The four ceramic magnets 27a are vertically stacked on nail 21a with unlike poles at their interfaces so as to magnetically attract each other. A set of four stacked magnets 27b and nail 21b similarly arranged are located adjacent nail 21a and magnets 27a with like poles between the adjacent sets facing one another so as to magnetically repel each other between sets. (A set of four magnets may have to be removed from the nail, turned 180° and replaced on the nail in order for this magnetic repulsion between sets to occur.) This process is repeated until all twenty sets of four magnets and one nail are in a 4×5 array, thus causing units 10 or 14 to magnetically adhere to the tips of each of the nails. The nails and their surrounding magnets are embedded in body 25 of non-metallic material, such as plastic, or of some suitable non-ferrous material, to a depth that covers the ceramic magnets. Member 22 may be a non-ferrous plate having twenty holes 28 therein through which nails 21 extend.

The FIG. 3 embodiment is used as follows: (1) Device 19 is moved toward tray 23 with probes 21 inserted into test receptacles 24 containing ferrous metal units 10 or 14 (not shown) which are to be treated, washed and transferred to reacting mixtures in other like test receptacles 24; (2) Device 19 is then lifted, with single units 10 or 14 adhering to each probe, and immersed into a bath for washing; (3) The magnetic probe device 19, with units adhering, is moved directly above another test receptacle tray 23 so that each well thereof underlies each probe, with each such well containing an appropriate solution for subsequent treatment of the units; (4) Member or shield 22 on the magnetic probe device is shifted relatively away from body 25, thereby causing individual units to drop into the appropriate wells of the solution-containing tray; (5) These or other combinations of manipulations can be repeated as required in the particular procedure being used.

FIG. 4 shows a second embodiment of a transfer device 29 of the present invention and shows an electromagnetic probe 31 as typical of several such probes which are embedded in and project outwardly of body 25 (not shown). Each probe 31 is capable of transferring at least one unit 10 or 14 which magnetically adheres thereto, and is provided in lieu of probe 21. And, associated with this device is a tray 23 having at least one test receptacle or well 24 for each electromagnetic probe.

A preferred embodiment of the transfer device of FIG. 4 includes a 4×5 array of six-penny common nails 31 having fifty turns of enameled armature wire 32 wrapped around the top end of each nail. Power is supplied by a battery 33 or by any other source of direct current. When a switch 34 is closed the nails become electromagnets, each capable of holding by magnetic force a unit to be treated, washed and transferred to another reaction mixture. Units are released by opening switch 34. The device illustrated in FIG. 4 is otherwise used in a manner similar to that described for the device illustrated in FIG. 3.

FIG. 5 illustrates a third embodiment of a transfer device of the present invention. This device 35 includes at least one ferrous metal probe 36 capable of transferring at least one unit 10 or 14 having a magnetic core which adheres to the probe, and a device 37 to remove the unit from the probe. Associated therewith is a tray 23 having at least one test receptacle or well 24 for each ferrous metal probe similarly as described in the FIG. 3 arrangement.

A preferred embodiment of transfer device 35 of FIG. 5 includes a plastic body 38 having twenty-four six-penny common finishing nails 36 projecting outwardly therefrom in a 4×6 array which are driven through a piece of wood 39 and embedded in body 38. Device 37 includes twenty-four pairs of ⅞"×5/16"×¼" rectangular ceramic magnets 40 (the pairs of magnets are located in the same configuration as the probes) held in place by a piece of sheet metal 42, both of which are embedded in plastic body 43, and two L-shaped pieces of metal 44 attached to the plastic body by adhesive bonding.

The embodiment illustrated in FIG. 5 may be used as follows:

(1) Probes 36 of device 35 are moved into wells 24 of tray 23 containing the specially coated magnetic units 10 or 14 which are to be treated, washed and transferred to other like trays or containers;

(2) Device 35 is lifted with the magnetic units adhering, and immersed into a bath for washing;

(3) Device 35, with the magnetic units adhering, is moved directly above another tray 23, each well 24 of which contains a solution for subsequent treatment of the units;

(4) The magnetic base 37 is slid under tray 23 and holds the tray in place by the two L-shaped pieces of metal 44 which engage opposite ends of the tray;

(5) Device 35 is again lowered until the units on each probe detach within the wells by the magnetic attraction of magnets 40;

(6) Device 35 is removed from tray 23 and the units remain in the wells thereof;

(7) These or other combinations of manipulations can be repeated as required in the particular procedure being used.

FIG. 6 shows a fourth embodiment of a transfer device 45 of the present invention, which is usable with tray 23. This apparatus includes either at least one probe comprising cylinder 46 of magnetic material capable of transferring at least one ferrous metal or magnetic unit 10, 14 which adheres to the probe, or at least one cylinder 46 of ferrous metal capable of transferring at least one magnetic unit 10, 14 or any combination thereof. Associated with this device is at least one test receptacle for every magnet or ferrous metal probe.

Transfer device 45 of FIG. 6 further includes a body 47 of insulating material such as plastic having imbedded therein twenty-four ¼"×¼" cylindrical ceramic magnets 46 in a 4×6 array. This device, as well as devices 19 and 35, may be coated with a substance such as epoxy paint 48 to prevent adsorption of the reactants to the apparatus and degradation of metallic components by solutions to which they are exposed, and a handle (not shown) may be added to assist in using any of the described devices.

The device shown in FIG. 6 is used as follows:

(1) Device 45 is placed over test receptacle tray 23 containing the units which are to be treated, washed and transferred to other trays of similar construction;

(2) Transfer device 45 is then lifted away from tray 23 with the units adhering to the transfer device;

(3) The transfer device and the adhering units are then immersed into a bath for washing;

(4) The transfer device with the units adhering, is moved directly above another tray 23, each well 24 of which contains a solution for subsequent treatment of the units;

(5) By sliding the transfer device across this tray, the units are wiped off and fall into the appropriate wells;

(6) These or other combinations of manipulations can be repeated as required in the particular procedure being used.

When test receptacle tray 23 is fabricated from a hydrophobic material such as polystyrene, and the well 24 diameter is under 7 mm, then surface tension is sufficient to retain the fluid in the receptacle even when the tray is inverted or abruptly pushed downward. The inversion or sudden downward push of the tray allows the unit to adhere to the probe but leaves the reaction fluid in the receptacle.

FIG. 7 illustrates a fifth embodiment of a transfer device 49 of the present invention. This device is identical to device 45 of FIG. 6 except that a wedge 51 is provided on body 47 and a block 52 having a slot 53 is provided on tray 54 which is otherwise identical to tray 23 of FIG. 5. Wedge 51 engages within slot 53 on the receptacle tray to allow centering or axial aligning and subsequent attachment of the transfer device to the test receptacle tray. FIG. 7A is a bottom plan view showing a part of device 49, and FIG. 7B is a top plan view showing a part of tray 54. The FIG. 7 device is used in a manner similar to that described for the transfer device shown in FIG. 6.

FIG. 8 illustrates a sixth embodiment of a transfer device of the present invention which includes transfer device 49 and tray 54 of FIG. 7. A body 55 of plastic material having at least one funnel-shaped hole 56 is provided. There are, of course, as many holes 56 provided as are cylinders 46 in the same configuration thereof. The top of the funnel is as wide or slightly wider than each cylinder 46, while the bottom of the funnel is as small or slightly smaller than each well 24 of the test receptacle tray. Body 55 assures that the unit will fall into the proper test receptacle well. Body 55 eliminates the problem of tranfer and delivery of the units between the transfer device and the test receptacle tray when the tray has been miniturized. Associated with each cylinder and funnel is at least one test receptacle well. Also, wedges 51 are provided on both device 49 and body 55 for engagement within slot 53 of block 52 similarly as in FIG. 7.

The device illustrated in FIG. 8 is used as follows:

(1) Device 45 is placed over test receptacle tray 23 containing the specially coated units which are to be treated, washed and transferred to other similar trays;

(2) Device 45 is then lifted away from tray 23 with the units adhering to the transfer device;

(3) Device 45 and the units are then immersed into a bath for washing;

(4) Device 45, with units adhering, is placed over body 55 which is disposed over another test receptacle tray, each well of the tray containing a solution for subsequent treatment of the units;

(5) By sliding device 45 across body 55, the units are wiped off and fall through funnels 56 and into the appropriate wells;

(6) These and other combinations of manipulations can be repeated as required in the particular procedure being used.

Obviously, many modifications and variations of the present invention are made possible in the light of the above teachings. Also, it should be pointed out that the devices described above may be used in carrying out assay methods employing non-radioactive markers or labels, such as various dyes or chemicals, which change colors upon reaction with other chemicals. It is therefore to be understood that within the scope of the appended claims the invention may be practiced otherwise than as specifically described.

What is claimed is:

1. A device for use in solid phase immumoassays, for simultaneously transferring a plurality of antigen-antibody absorbent units from one location to another, comprising a transfer element in combination with a tray of non-magnetic material having a plurality of spaced receptacles therein for containing an appropriate liquid and for containing units each comprising a core of ferromagnetic material, each said core being covered with at least one coating for preventing chemical interactions between said core and aqueous chemical solutions and for absorbing antigens or antibodies on the outer surface thereof, said transfer element having a first portion of ferromagnetic material overlying said spaced receptacles in a transfer condition of said element, and said element having a second portion of non-magnetic material overlying spaces between said receptacles when in said transfer condition, and one of said ferromagnetic core and transfer device materials having magnetic properties to effect a magnetic attraction between said units and said transfer device, whereby said units are removable from said receptacles by magnetic attraction while being maintained in spaced apart relationship by said non-magnetic material during said transfer condition.

2. The device according to claim 1, wherein cooperating means are provided on said tray and on said transfer element for effecting said aligned condition therebetween.

3. The device according to claim 1, wherein said ferromagnetic material of said transfer element comprise a plurality of ferromagnetic elements spatially oriented relative to said spaced receptacles.

4. The device according to claims 1, 2 or 3, wherein each said unit has an inner coating for preventing chemical interactions between said core and the aqueous chemical solutions and an exterior coating for adsorbing antigens or antibodies on said outer surface thereof.

5. The device according to claim 4, wherein said exterior coating comprises an adsorbing coat selected from the group consisting of polycarbonate, polyethylene, polystyrene, polypropylene, acrylics, glass and chromatographic substances.

6. The device according to claim 4, wherein said inner coating includes a stable metal selected from the group consisting of nickel, gold, zinc, chromium, cadmium and copper, for effectively sealing said core from penetration and chemical interaction with aqueous chemical solutions.

7. The device according to claim 6, wherein said exterior coating comprises an adsorbing coat selected from the group consisting of polycarbonate, polyethylene, polystyrene, polypropylene, acrylics, glass and chromatographic substances.

8. The device according to claim 4, wherein said inner coating comprises waterproof paint material for effectively sealing said core from penetration and chemical interaction with the aqueous chemical solutions.

9. The device according to claim 8, wherein said exterior comprises an adsorbing coat selected from the group consisting of polycarbonate, polyethylene polystyrene, polypropylene, acrylics, glass and chromatographic substances.

10. The device according to claims 1, 2, or 3, wherein said transfer element is at least partially coated with a material capable of reducing or preventing adsorption of antibodies or antigens to its surface and of preventing degradation of said non-magnetic material of said transfer element during exposure to aqueous chemical solutions used in solid phase immunoassays.

11. The device according to claim 3, wherein said ferromagnetic elements are disposed flush with a surface of said transfer element.

12. The device according to claim 3, wherein said ferromagnetic elements extend outwardly of a surface of said transfer element, and a release member of non-magnetic material surrounding said ferromagnetic elements is provided for releasing said units adhering thereto by movement of said release member away from said surface.

* * * * *

UNITED STATES PATENT OFFICE
CERTIFICATE OF CORRECTION

PATENT NO. : 4,292,920

DATED : October 6, 1981

INVENTOR(S) : KENDALL O. SMITH and WARREN D. GEHLE

It is certified that error appears in the above-identified patent and that said Letters Patent are hereby corrected as shown below:

In the title page, correct the related U.S. Application Data to read "Division of Serial No. 680,506, April 26, 1976, now U.S. Patent No. 4,272,510."

Signed and Sealed this

Twenty-fourth Day of August 1982

|SEAL|

Attest:

GERALD J. MOSSINGHOFF

*Attesting Officer*     *Commissioner of Patents and Trademarks*